(12) United States Patent
Muthuvelan

(10) Patent No.: US 6,651,279 B1
(45) Date of Patent: Nov. 25, 2003

(54) METHOD AND APPARATUS FOR COLLISION AVOIDANCE IN A PATIENT POSITIONING PLATFORM

(75) Inventor: Varadharajulu Muthuvelan, Chennai, IN (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 10/248,859

(22) Filed: Feb. 25, 2003

Related U.S. Application Data (60) Provisional application No. 60/429,283, filed on Nov. 26, 2002.

(51) Int. Cl.$^7$ .................................................. A47B 7/02
(52) U.S. Cl. ................................................ 5/600; 5/601
(58) Field of Search ........................... 5/600, 601, 607, 5/611

(56) References Cited

U.S. PATENT DOCUMENTS

| | | | |
|---|---|---|---|
| 4,541,108 A | | 9/1985 | Grady et al. |
| 4,576,368 A | * | 3/1986 | Ogawa et al. .................. 5/611 |
| 4,715,591 A | | 12/1987 | Dragmen |
| 4,761,000 A | | 8/1988 | Fisher et al. |
| 4,769,584 A | * | 9/1988 | Irigoyen et al. ............ 318/648 |
| 4,912,754 A | | 3/1990 | Van Steenburg |
| 5,048,071 A | | 9/1991 | Van Steenburg |
| 5,156,166 A | | 10/1992 | Sebring |
| 5,205,004 A | | 4/1993 | Hayes et al. |
| 5,572,569 A | | 11/1996 | Benoit et al. |
| 6,038,718 A | * | 3/2000 | Pennington et al. ........... 5/618 |
| 6,269,499 B1 | | 8/2001 | Amir |
| 6,353,949 B1 | | 3/2002 | Falbo |

FOREIGN PATENT DOCUMENTS

EP 268 555 B1 10/1986

* cited by examiner

*Primary Examiner*—Teri Pham Luu
*Assistant Examiner*—Fredrick Conley
(74) *Attorney, Agent, or Firm*—McAndrews, Held & Malloy, Ltd.; Peter J. Vogel; Michael A. Dellapenna (57) ABSTRACT

Certain embodiments include a system and method for collision avoidance in a patient positioning system. The system includes a patient positioning surface, a position sensor for determining a position of the patient positioning surface, and a control subsystem for controlling operation of the patient positioning system. The control subsystem dynamically determines a clearance distance between the patient positioning surface and the object. The control subsystem halts motion of the patient positioning surface if the clearance distance is less than or equal to a minimum safe clearance distance. The control subsystem may dynamically determine the clearance distance before, during, and/or after motion of the patient positioning surface. The method includes determining a clearance distance between the patient positioning surface and an object, comparing the clearance distance to a minimum safe clearance distance, and halting motion of the patient positioning surface if the clearance distance is less than or equal to the minimum safe clearance distance.

20 Claims, 5 Drawing Sheets

Up-Down & Rotation (Patient Loading)

Longitudinal Travel (Scanning)

Longitudinal Tilt (Vascular Tilt)

FIG. 3

Highest Postion

Lowest Postion

Fwd. Tilt Position

Reverse Tilt Position

FIG. 4

HEAD - DOWN TILT

HEAD - UP TILT

ISO-CENTER TRACKING

Figure 5

METHOD AND APPARATUS FOR COLLISION AVOIDANCE IN A PATIENT POSITIONING PLATFORM

CROSS REFERENCE TO RELATED APPLICATIONS

The present application relates to, and claims priority from, U.S. Provisional Application No. 60/429,283 filed on Nov. 26, 2002, and entitled "Method and Apparatus for Collision Avoidance in a Patient Positioning Platform".

BACKGROUND OF INVENTION

The present invention generally relates to collision avoidance in a patient positioning platform. In particular, the present invention relates to dynamically calculating clearance for collision avoidance in a patient positioning platform.

Patient positioner platforms allow a medical practitioner, such as a doctor, nurse or technician, to position a patient during a medical procedure, such as XR, CT, EBT, nuclear, and PET procedures. Patient positioner platforms, such as tables or other supports, allow a patient to be elevated, moved in lateral & longitudinal directions, rotated and/or tilted during a procedure. Patient positioning platforms improve a medical practitioner's ability to examine and/or perform a medical procedure on a patient.

There is a need for an improved patient positioning platform that may be used in angiography, neurology, and cardiac procedures. Current patient positioner platforms may introduce limitations in obtaining images of blood flow in arteries, heart, lungs, or brain, for example. Thus, a patient positioning system that improves stability and reliable positioning for blood flow imaging in angiography, neurology, cardiac and other such procedures would be highly desirable. Additionally, a patient positioning system that provides reliable and easy positioning of a patient with flexibility to accommodate a variety of medical procedures and emergencies would be highly desirable.

An improved patient positioning platform is capable of performing complex motions to position a patient. During such complex motions, the patient positioning platform may hit the ground or another object. A collision may cause injury to the patient and/or the patient positioning platform. Additionally, a collision may disrupt system calibration and result in faulty measurements or image scans.

Thus, a need exists for a method and system to determine a clearance distance to avoid a collision between a patient positioning platform and the ground or another object.

SUMMARY OF INVENTION

Certain embodiments include a system and method for collision avoidance in a patient positioning system. The system includes a patient positioning surface for supporting a patient, a lift subsystem for adjusting elevation of the patient positioning surface, a longitudinal subsystem for moving the patient positioning surface in a longitudinal direction, a tilt subsystem for tilting the patient positioning surface, a position sensor for determining a position of the patient positioning surface, and a control subsystem for controlling operation of the patient positioning system. The control subsystem dynamically determines a clearance distance between the patient positioning surface and the object. The control subsystem halts motion of the patient positioning surface if the clearance distance is less than or equal to the minimum safe clearance distance.

The control subsystem may dynamically determine the clearance distance before, during, and/or after motion of the patient positioning surface. The control subsystem may also halt motion of the patient positioning surface if the clearance distance is equal to the minimum safe clearance distance. The position sensor may include an encoder for determining the position of the patient positioning surface. The position sensor may allow the patient positioning surface to return to a recorded position. Certain embodiments may include a plurality of position sensors determining a position of the patient positioning surface along a plurality of axes of motion.

Certain embodiments also include a lateral subsystem for moving the patient positioning surface in a lateral direction. The system may also include a rotation subsystem for rotating the patient positioning surface. At least one brake may be used to halt motion of the patient positioning surface.

The method includes determining a clearance distance between a current position of the patient positioning surface and an object to be avoided. The method also includes comparing the clearance distance to a minimum safe clearance distance and halting motion of the patient positioning surface if the clearance distance is less than or equal to the minimum safe clearance distance.

The method may also include determining the minimum safe clearance distance to avoid a collision with the object to be avoided. The method may further include halting motion of the patient positioning surface if the clearance distance is equal to the minimum safe clearance distance. Additionally, the method may include moving the patient positioning surface to a desired position. The method may include measuring the current position of the patient positioning surface using a position sensor. The current position of the patient positioning surface may be measured with respect to a plurality of axes of motion. The plurality of axes of motion may include at least one of tilt, longitudinal, and lateral axes.

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION

Figure 1:
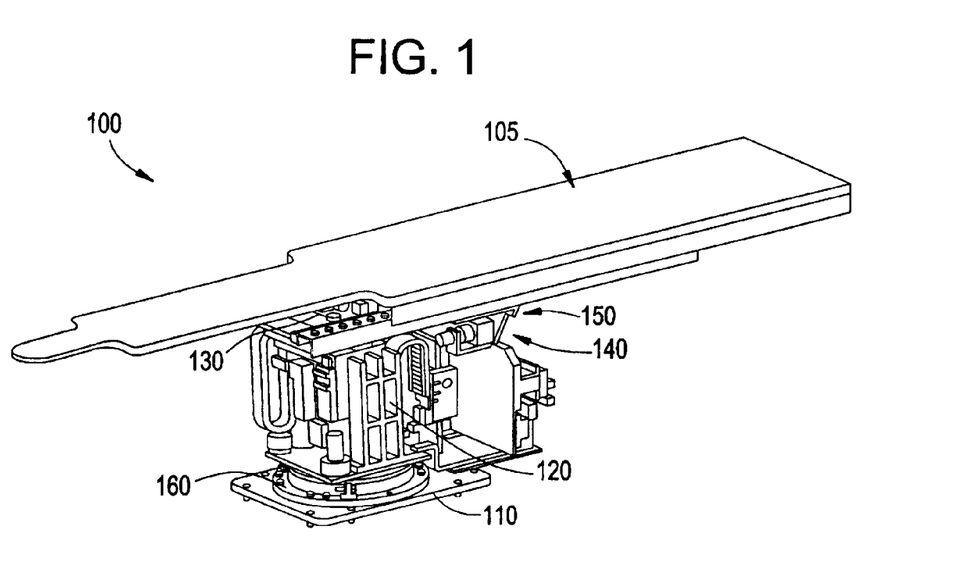
FIG. 1 illustrates a patient positioning system that is used in accordance with an embodiment of the present invention.

FIG. 1 illustrates a patient positioning system 100 that is used in accordance with an embodiment of the present invention. The patient positioning system 100 includes a patient positioning surface 105, a base 110, a telescopic lift system 120, a longitudinal system 130, a tilt system 140, a lateral system 150 and a rotation system 160. The patient positioning system 100 is grouted, or fixed to the floor at the table base 110. The system 100 also includes a motion control system 170 (not pictured). The patient positioning system is described in more detail in U.S. Patent Application entitled "Grouted Tilting Patient Positioning Table for Vascular Applications," (application Ser. No. 10/065,866), filed on Nov. 26, 2002, with inventors Muthuvelan Varadharajulu, Rajagopal Narayanasamy, Baskar Somasundaram, and Shaji Alakkat. The application is herein incorporated by reference including the specification, drawings, claims, abstract, and the like.

Figure 2:
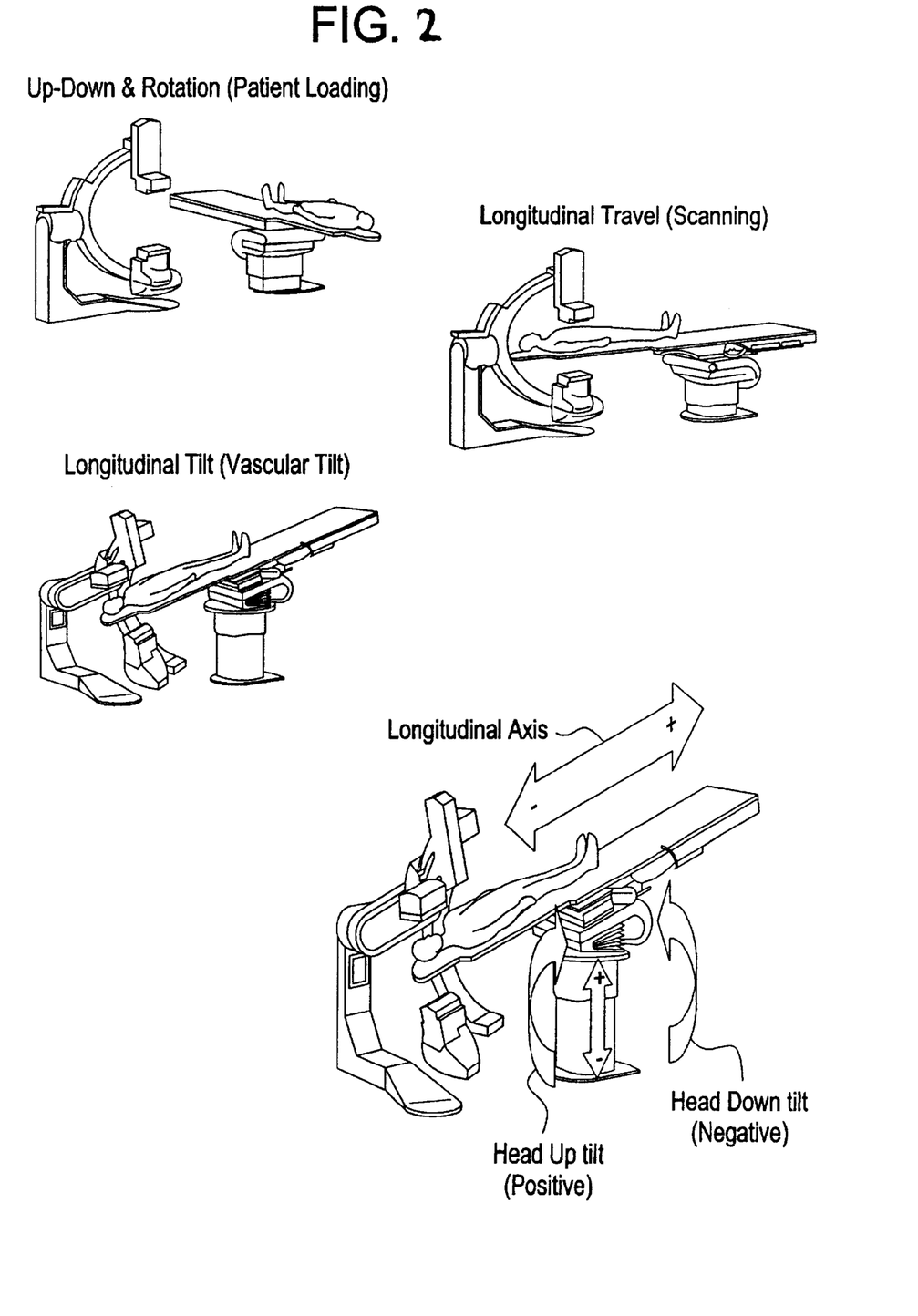
FIG. 2 illustrates positions of a patient positioning surface used in accordance with an embodiment of a present invention.
Figure 3:
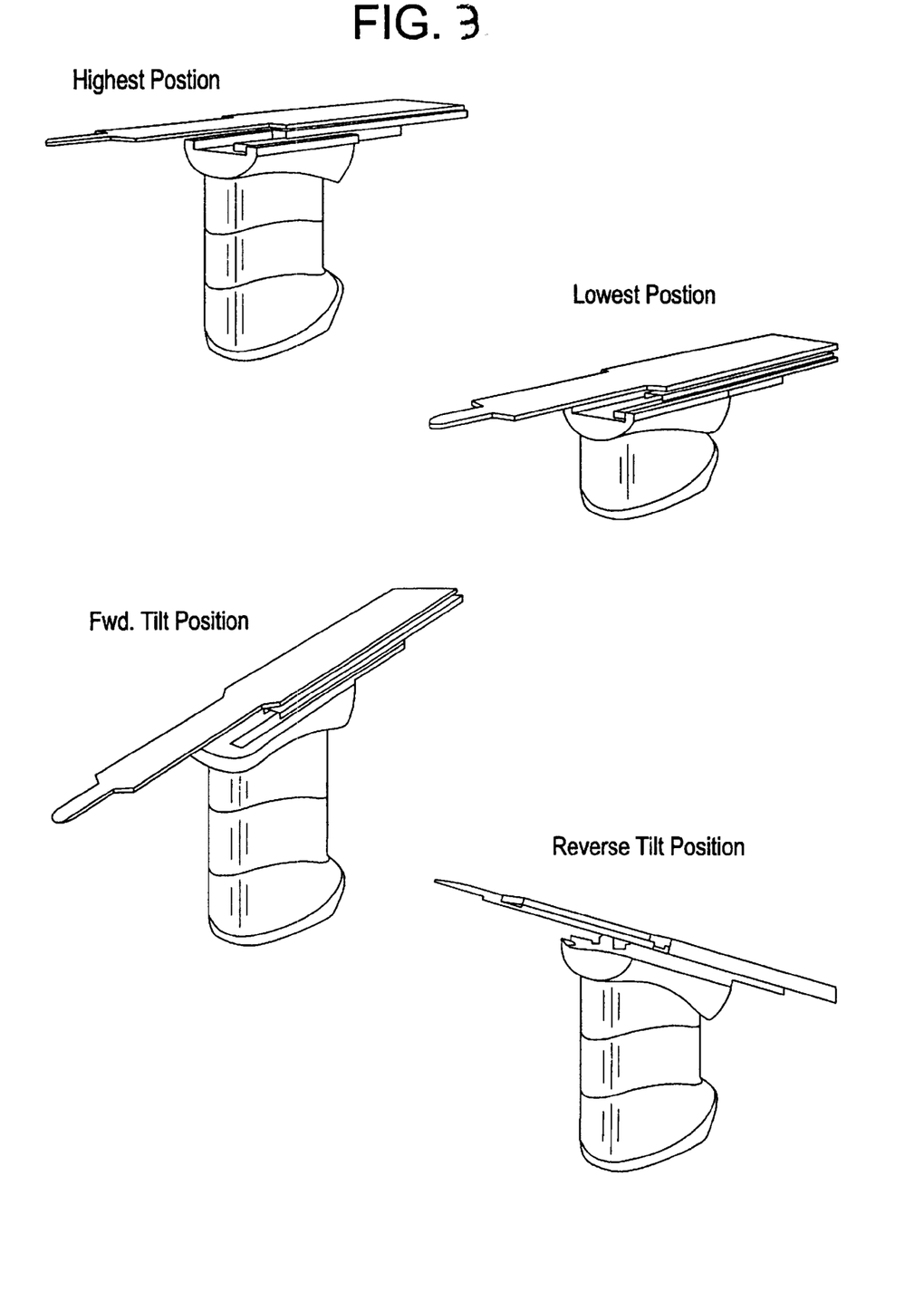
FIG. 3 illustrates positions of a patient positioning surface used in accordance with an embodiment of the present invention.

To enhance loading and unloading of a patient, the patient positioning surface 105 may rotate around a vertical axis using the rotation system 160. The patient positioning surface 105 may also be manually rotated about the rotation system 160. To move the patient to an image area, the patient positioning surface 105 may move vertically using the telescopic lift system 120 from a height at which the patient may be conveniently loaded to a height where imaging may occur (780 mm to 1080 mm, for example). To move a portion of the patient's body into the image area, the patient positioning surface 105 may move in a lateral direction (+/−140 mm from a normal imaging position, for example) using the lateral system 150. FIGS. 2 and 3 illustrate exemplary positions of the patient positioning surface 105 used in accordance with certain embodiments of the present invention.

Figure 4:
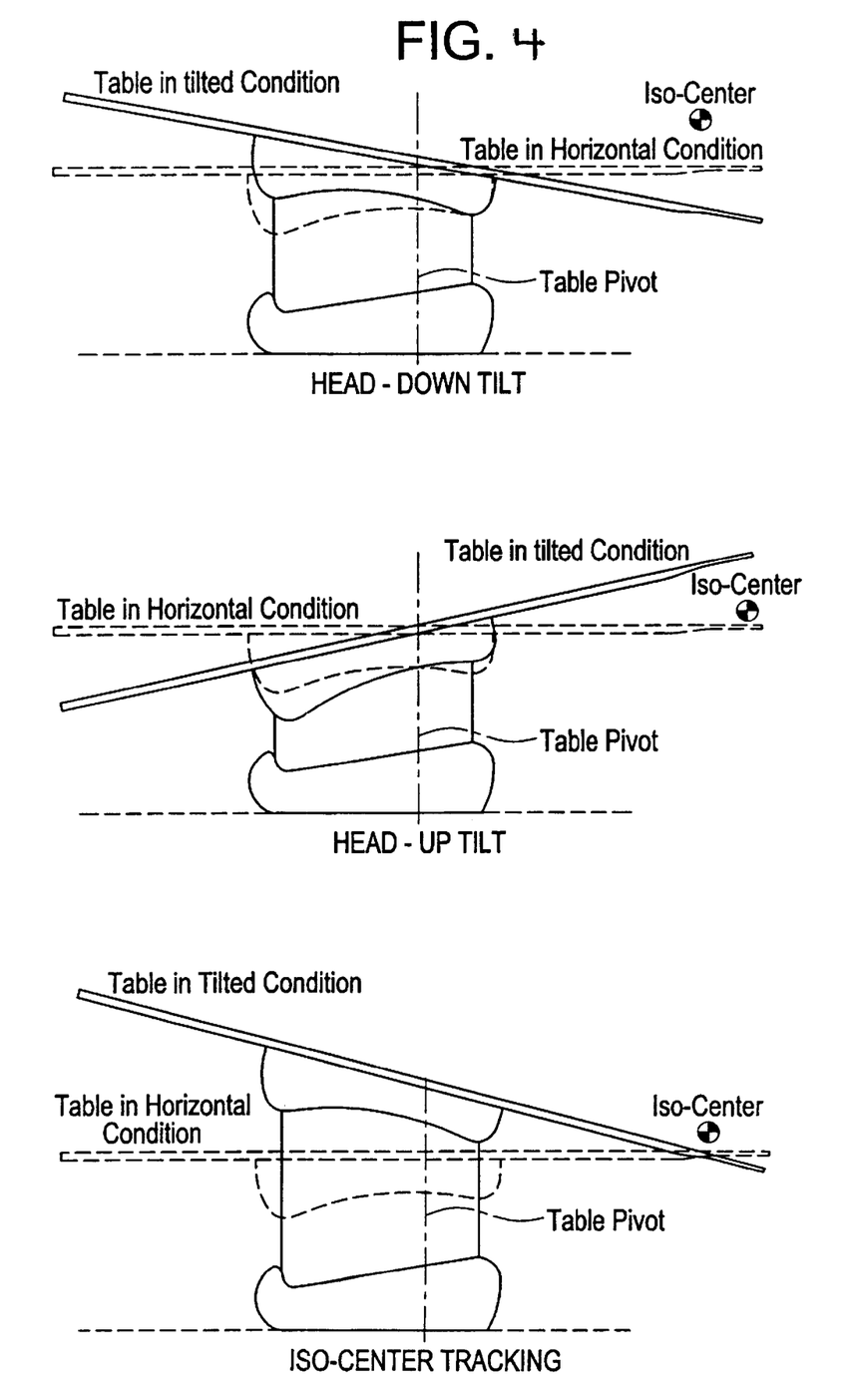
FIG. 4 depicts a tilting of a patient positioning surface with and without iso-center tracking used in accordance with an embodiment of the present invention.

Additionally, the telescopic lift system 120 may provide a stroke or lift motion for iso-center tracking. Iso-center is the point at which three axes of an x-ray imaging system gantry meet (not shown). Iso-center tracking maintains a patient region of interest at the iso-center during tilt or other movement of the patient positioning system 100. Additional stroke for iso-center tracking is provided by the telescopic lift system 120 supported by a telescopic guide mechanism to accommodate a moment resulting from overhanging load. FIG. 4 depicts a tilting of the patient positioning surface 105 with and without iso-center tracking used in accordance with an embodiment of the present invention.

For head to toe coverage of the patient, the patient positioning system 100 may use longitudinal motion from the longitudinal system 130. For bolus chasing (following a bolus or contrast agent through a patient's blood vessels), the longitudinal motion may be motorized with a variable speed motor (2 to 15 cm/sec, for example) using the longitudinal system 130 and a guide mechanism. In a certain embodiment, in addition to motorized motion, lateral and longitudinal axes include a clutch to support manual panning of the patient positioning surface 105. That is, the clutch may be released to allow the patient positioning surface 105 to be positioned manually by an operator.

For emerging vascular procedures, such as emergent situations (falling artery pressure, for example), venous access and $CO_2$ studies, the patient positioning surface 105 may tilt head up and head down in the longitudinal direction (12 degrees up and 20 degrees down, for example). A region of interest of the patient may remain at the iso-center or the image area when the patient positioning surface 105 is tilted. In an embodiment, the region of interest remains in the iso-center or the image area using synchronized motion of the telescopic lift system 120, the longitudinal system 130 and the tilt system 140 as defined by the Inverse Kinematics Formula.

In an embodiment, mechanical and electrical interlocks and position feedback from the patient positioning system 100 help to ensure patient safety. Patient restraints may be provided to keep the patient on the patient positioning surface 105 and to help ensure patient safety. Certain embodiments of the patient positioning system 100 help to ensure a high level of patient safety through effective safety interlock systems and redundant systems for avoiding single point failures.

Safety interlocks and redundant safety systems are provided to help ensure patient safety in the patient positioning system 100. In an embodiment, all axes in the patient positioning system 100 are designed to have position encoders to read the coordinates of the patient positioning surface 105 at any position at any time. Ground clearance of the patient positioning surface 105 is calculated, and motion of the patient positioning surface 105 stops if the ground clearance is less than or equal to a specified safe limit. Thus, collisions may be avoided.

In a certain embodiment, all axes are designed with redundant safety systems to avoid single point failures and to help ensure patient safety. Each motorized axis of the patient positioning system 100 may include an incremental encoder and brake (on the drive or motor side). Each motorized axis may also include an absolute encoder and brake at the load side. During normal operation, the brake at the drive side operates to stop any axis of motion. If a problem arises in the driveline, a difference in incremental encoder (drive side) and absolute encoder (load side) readings operates the brake at the load side to stop the axis. Additionally, as described above, both power-on and power-off brakes may be activated during procedures to ensure stability and rigidity of the patient positioning surface 105. During power-off conditions, only the power-off brake is activated to allow easy removal of the patient by rotating the patient positioning surface 105.

In an embodiment, the patient positioning surface 105 may be prevented from tilting at the lowest position of the patient positioning surface 105, since the lowest position of the patient positioning surface 105 is for easy loading and unloading of the patient. Each axis is provided with a power-off brake to lock the motion during a power failure and/or any malfunction of the motors and servo drives. Each axis is provided with a software limit, a hardware limit, and mechanical hard stops. An example of a software limit is the following: during normal operations, the patient positioning surface 105 shall not move beyond a certain point. An example of a hard limit is the following: the patient positioning surface 105 is controlled by a limit switch. The limit switch stops the motion of the patient positioning surface 105 if a software malfunction occurs. An example of a mechanical hard stop is as follows: an end stop is provided as backup if both software and hardware limits fail. The coordinates of all axes may be continuously monitored to avoid a collision with the ground and/or predetermined objects.

The following are some examples of operations involving the patient positioning system 100. The examples are provided to illustrate the use of components and systems in the patient positioning system 100 and are not intended to be a comprehensive list.

For example, a patient may be loaded on the patient positioning surface 105. First, the patient positioning surface 105 is positioned at 780 mm from the ground using the telescopic lift system 120. Then, the patient positioning surface 105 is rotated to the right-hand or left-hand side using the rotation system 160. Next, the patient is loaded onto the patient positioning surface 105. Patient restraints may be used to secure the patient on the patient positioning surface 105. To unload the patient, the patient positioning surface 105 is rotated to the right-hand or left-hand side using the rotation system 160. The patient positioning surface 105 is repositioned to a height of 780 mm from ground level by the lift system 120. The patient restraints are unlocked, and the patient is removed from the patient positioning surface 105.

Also, for example, the patient may be moved into the image area. First, the rotation system 160 rotates the patient positioning surface 105 to zero degree. Next, the patient positioning surface 105 is moved vertically to the image area using the telescopic lift system 120. Then, the patient positioning surface 105 is adjusted laterally in the image area with the lateral system 150. The patient positioning surface 105 may also be adjusted longitudinally by the longitudinal system 130 to reach a desired position in the image area.

A patient may be positioned on the patient positioning surface 105 for several medical procedures and examinations. For example, in angiography, a patient's height may be adjusted by raising and lowering the patient positioning surface 105 using the telescopic lift system 120. Additionally, four-way panning may be accomplished using the lateral system 150 and the longitudinal system 130. For peripheral angiography, the patient positioning surface 105 may also be rotated into proper position using the rotation system 160 and tilted using the tilt system 140.

For bolus chasing, patient restraints may be used to secure the patient on the patient positioning surface 105. The longitudinal system 130 advances the patient positioning surface 105 in the longitudinal direction in bolus mode (0–15 cm/sec). For venous access and $CO_2$ studies, for example, patient restraints may keep the patient in touch with the patient positioning surface 105, and the lift 120, longitudinal 130, and tilt 140 systems may be used for iso-center tracking to maintain a desired image area during movement. In emergent situations, restraints secure the patient on the patient positioning surface 105, and the tilt system 140 tilts the patient to a desired position.

Cardiac pulmonary resuscitation (CPR) is a procedure performed for patients who suffer from cardiac arrest, for example. In order to bring a patient to a CPR position if the patient positioning surface 105 is in a horizontal position, the patient positioning. surface 105 is moved longitudinally in a backward direction using the longitudinal system 130. Then, the patient positioning surface 105 is lowered using the lift system 120. If the patient positioning surface 105 is titled, the tilt system 140 returns the patient positioning surface 105 to a horizontal position. Then, the longitudinal system 130 moves the patient positioning surface 105 backward, and the lift system 120 lowers the patient positioning surface 105 to enable CPR to be performed on the patient.

The telescopic lift system 120 is used by the patient positioning system 100 to accommodate high load, moments, and lift motion or stroke to position a patient in the image area. The tilt system 140 allows the patient positioning system 100 to tilt head up or head down and maintain a desired image through iso-center tracking. The patient positioning system 100 includes a lateral system 150 to move the patient positioning surface 105 laterally using motorized and/or manual panning.

The patient positioning system 100 supports motorized bolus chasing with head to toe coverage so that an image may be traced as the contrast agent travels through the patient. The patient positioning system 100 tracks the coordinates of the patient positioning surface 105. Positioning tracking facilitates collision avoidance with the ground and/or other predetermined objects. Tracking also allows the patient positioning system 100 to return the patient positioning surface 105 to a previously recorded and/or memorized position.

Examples of complex motion of the patient positioning system 100 have been described above. Execution of complex motions to position the patient positioning surface 105 for various medical procedures creates a risk of collision between the patient positioning surface 105 and the ground and/or another object in the examination room. Certain embodiments of the present invention provide a system and method for collision avoidance.

The motion control system 170 for the patient positioning system 100 includes three major parts: a user interface, an I/O board, and servo nodes (not shown). A user may move the patient positioning surface 105 using the user interface. User interface commands are processed by the I/O board (CPU). Commands are then sent to corresponding servo nodes that control the respective axis movements. In an embodiment, a power PC-based micro controller is used as the CPU. An application program, which is running on a real-time operating system, may control the patient positioning system 100.

Clearance between the patient positioning surface 105 and the ground and/or another object is determined dynamically based on the positions of the lift, longitudinal, and tilt axes in the patient positioning system 100. The motion control system 170 may store a safe clearance value. The motion control system 170 determines the clearance between the patient positioning surface 105 and the ground or another object. The motion control system 170 compares the measured clearance and the safe clearance value. The motion control system 170 stops the movements of the axes of the patient positioning system 100 if the measured clearance is less than or equal to the stored safe clearance.

The motion control system 170 may determine clearance for collision avoidance for all axes (lift, longitudinal, tilt, for example). Clearance may be determined for any combination of the axes of movement (one axis alone, two axes together, and/or three axes together, for example). The motion control system 170 determines clearance and a safe position for the patient positioning surface 105 to avoid a collision with the ground or another object. The motion control system 170 may determine clearance dynamically at any time during operation of the patient positioning system 100. Current systems do not determine clearance in this manner.

In an embodiment, the clearance of the patient positioning surface 105 has two components. A first component is a distance between the front of the patient positioning surface 105 and an object to be avoided (such as the ground). A second component is a distance between the rear of the patient positioning surface 105 and an object to be avoided. The first clearance component is determined using the following equation:

$$Y_{gf} = [(X_1 - C_3) + ((C_3 - C_4) * \cos X_2) - C_7] + [(C_2 - X_3) * \sin X_2] \quad (1).$$

The second clearance component is determined using the following equation:

$$Y_{gr} = [(X_1 - C_3) + ((C_3 - (C_5 + C_6)) * \cos X_2) - C_7] - [(C_1 + X_3 - C_2) * \sin X_2] \quad (2)$$

The following description is an example of the collision avoidance system in operation. The numbers are for illustration purposes. The length of the patient positioning surface 105 (also known as the cradle) is $C_1=3336.00$ mm. The length of the portion of the patient positioning surface 105 that extends from a pivot point of the tilt system 140 when the patient positioning surface 105 is fully retracted is $C_2=1226.00$ mm. The vertical height between the patient positioning surface 105 and the pivot point of the tilt system 140 $C_3=244.00$ mm. The thickness of the front of the patient positioning surface 105 is $C_4=20.00$ mm. The thickness of the rear of the patient positioning surface 105 is $C_5=41.00$ mm. The height of the sliding mechanism of the longitudinal system 130 is $C_6=70.50$ mm. A safe clearance distance or minimum height to be maintained is $C_7=45.00$ mm. The position of the patient positioning surface 105 at the lift axis at any given time is read from an encoder or other position sensor, for example, on the lift system 120. For example, the lift axis position is $X_1=1080.00$ mm. A tilt angle is read from current tilt axis position via an encoder or other position sensor, for example, in the tilt system 140. For example, the tilt angle is $X_2=-16.00$ degrees (head up angle is positive; head down angle is negative). The position of the patient positioning surface 105 in the longitudinal axis at any given time is read from the current longitudinal axis position (such as from an encoder in the longitudinal system 130). A negative position indicates motion towards a gantry in a medical imaging system. For example, $X_3=-1700.00$ mm. Using the above measurements in equations (1) and (2) yields a front clearance of $Y_{gf}=199.81$ mm and a rear clearance of $Y_{gr}=1031.38$ mm from the ground. Since both measurements are greater than the minimum safe distance of 45.00 mm, motion of the patient positioning surface 105 may be allowed.

Figure 5:
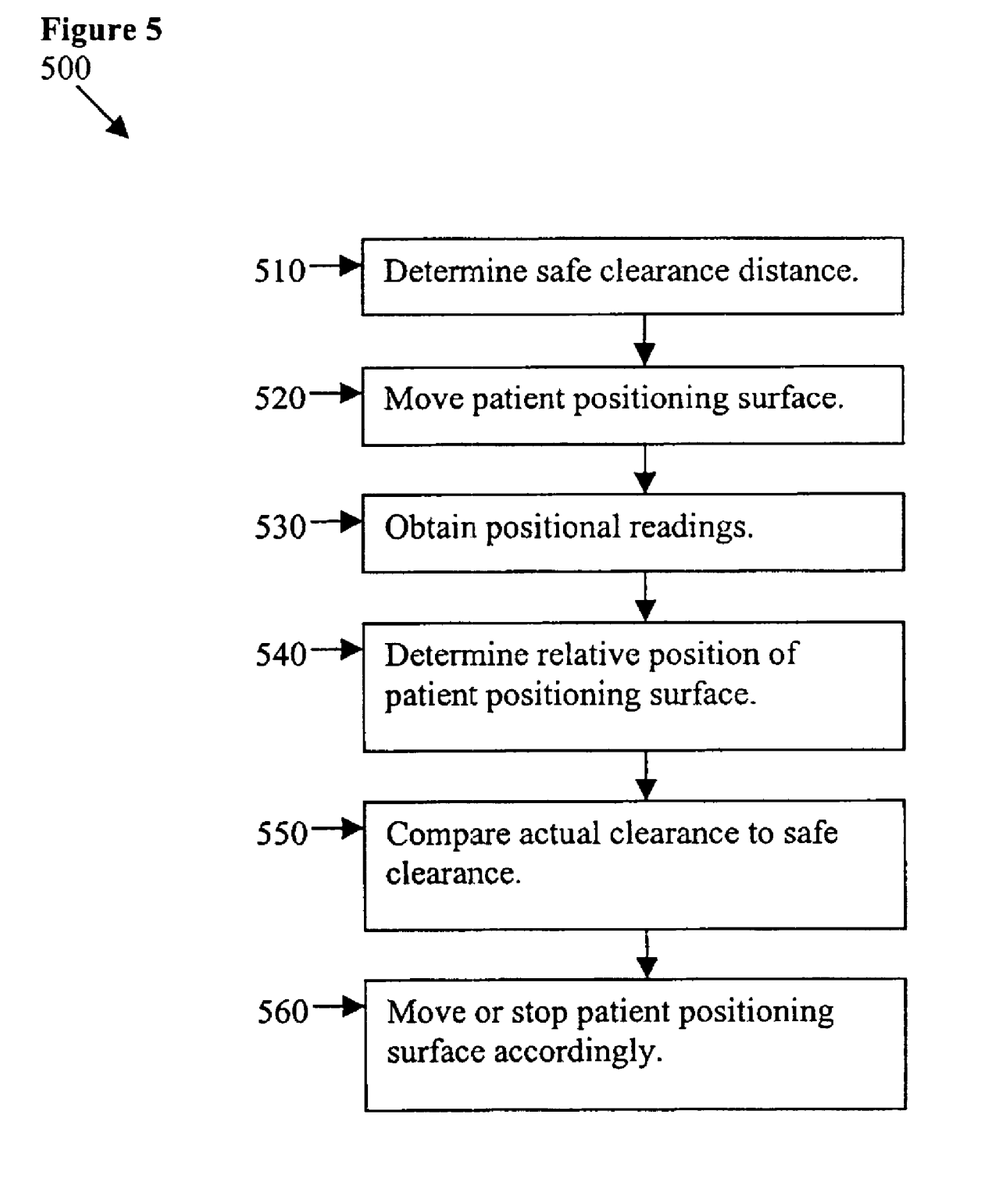
FIG. 5 shows a flow diagram for a method for position avoidance in a patient positioning system used in accordance with an embodiment of the present invention.

FIG. 5 shows a flow diagram 500 for a method for position avoidance in a patient positioning system used in accordance with an embodiment of the present invention. First, at step 510, a safe clearance distance is determined that will allow the patient positioning surface 105 to maneuver normally without a risk of injury to the patient or introduction of error in imaging, for example, from a collision. The minimum safe distance is stored in the system 100 for reference in triggering collision avoidance.

Then at step 520, the patient positioning surface 105 is moved to a desired position. At step 530, while the patient positioning surface 105 is moving, positional readings are obtained by encoders, for example, on the axes of motion (tilt, lift, longitudinal, for example). Positional readings may be obtained before, during, and/or after movement of the patient positioning surface 105. Next, at step 540, the positional readings are used to determine the position of the patient positioning surface 105 in relation to an object, such as the floor.

Then, at step 550, the position of the patient positioning surface 105 is compared to the safe clearance distance. If the actual clearance is greater than the safe clearance, then the patient positioning surface 105 may be moved. At step 560, if the actual clearance is less than or equal to the safe clearance, then motion of the patient positioning surface 105 is stopped. The patient positioning surface 105 may be moved in a direction with a clearance distance greater than the minimum safe clearance distance. A user interface, for example, may be used to initiate movement of the patient positioning surface 105.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

What is claimed is:

1. A patient positioning system for medical applications, said system comprising:
    a patient positioning surface for supporting a patient;
    a lift subsystem for adjusting elevation of said patient positioning surface;
    a longitudinal subsystem for moving said patient positioning surface in a longitudinal direction;
    a tilt subsystem for tilting said patient positioning surface;
    a position sensor for determining a position of said patient positioning surface; and
    a control subsystem for controlling operation of said patient positioning system, said control subsystem dynamically determining a clearance distance between said patient positioning surface and an object, said control subsystem halting motion of said patient positioning surface if said clearance distance is less than or equal to a minimum safe clearance distance.

2. The system of claim 1, wherein said control subsystem dynamically determines said clearance distance at least one of before, during, and after motion of said patient positioning surface.

3. The system of claim 1, wherein said control subsystem halts motion of said patient positioning surface if said clearance distance is equal to said minimum safe clearance distance.

4. The system of claim 1, wherein said position sensor comprises an encoder for determining said position of said patient positioning surface with respect to said object.

5. The system of claim 1, wherein said position sensor allows said patient positioning surface to return to a recorded position.

6. The system of claim 1, further comprising a plurality of position sensors determining a position of said patient positioning surface along a plurality of axes of motion.

7. The system of claim 1, further comprising a lateral subsystem for moving said patient positioning surface in a lateral direction.

8. The system of claim 1, further comprising a rotation subsystem for rotating said patient positioning surface.

9. The system of claim 1, further comprising at least one brake to halt motion of said patient positioning surface.

10. A method for dynamic collision avoidance in a patient positioning system, said method comprising:
    determining a clearance distance between a current position of a patient positioning surface and an object to be avoided;
    comparing said clearance distance to a minimum safe clearance distance; and halting motion of said patient positioning surface if said clearance distance is less than or equal to said minimum safe clearance distance.

11. The method of claim 10, further comprising determining said minimum safe clearance distance to avoid a collision with said object to be avoided.

12. The method of claim 10, further comprising halting motion of said patient positioning surface if said clearance distance is equal to said minimum safe clearance distance.

13. The method of claim 10, further comprising moving said patient positioning surface to a desired position.

14. The method of claim 10, further comprising measuring said current position of said patient positioning surface using a position sensor.

15. The method of claim 10, further comprising measuring said current position of said patient positioning surface with respect to a plurality of axes of motion.

16. The method of claim 15, wherein said plurality of axes of motion include at least one of tilt, longitudinal, and lateral axes.

17. A patient positioning system with dynamic collision avoidance, said system comprising:

a patient positioning surface for supporting a patient;

at least one position sensor for determining a position of said patient positioning surface along at least one axis of motion; and a control subsystem for controlling operation of said patient positioning system, said control subsystem dynamically determining a clearance distance between said patient positioning surface and an object to be avoided, said control subsystem halting motion of said patient positioning surface if said clearance distance is less than or equal to a minimum safe clearance distance.

18. The system of claim 17, wherein said control subsystem dynamically determines said clearance distance at least one of before, during, and after motion of said patient positioning surface.

19. The system of claim 17, further comprising at least one brake for halting motion of said patient positioning surface.

20. The system of claim 17, further comprising a user interface for directing motion of said patient positioning surface.

* * * * *